United States Patent
Mason et al.

(10) Patent No.: US 8,849,572 B2
(45) Date of Patent: Sep. 30, 2014

(54) APPARATUS FOR DETERMINING THE CONCENTRATION OF A CONDUCTIVE FLUID PRESENT IN A FLUID FILLED BOREHOLE

(75) Inventors: Guy Harvey Mason, Hampshire (GB); James Andrew Gulliver, Oxfordshire (GB); Derek George Hayes, Berkshire (GB); Paul Franklin Steel, Berkshire (GB); Kenneth Tomkins, Berkshire (GB); Andrew John Stevens, Hampshire (GB)

(73) Assignee: Sondex Wireline Limited, Yateley (GB)

( * ) Notice: Subject to any disclaimer, the term of this patent is extended or adjusted under 35 U.S.C. 154(b) by 1000 days.

(21) Appl. No.: 12/663,098

(22) PCT Filed: Jun. 6, 2008
(Under 37 CFR 1.47)

(86) PCT No.: PCT/GB2008/001979
§ 371 (c)(1),
(2), (4) Date: May 17, 2010

(87) PCT Pub. No.: WO2008/149124
PCT Pub. Date: Dec. 11, 2008

(65) Prior Publication Data
US 2010/0299068 A1 Nov. 25, 2010

(30) Foreign Application Priority Data
Jun. 8, 2007 (GB) .................................. 0711096.8

(51) Int. Cl.
| | |
|---|---|
| *G01V 3/18* | (2006.01) |
| *G01V 3/34* | (2006.01) |
| *G01V 3/38* | (2006.01) |
| *G06F 3/00* | (2006.01) |
| *E21B 47/10* | (2012.01) |
| *G01N 27/07* | (2006.01) |
| *G01N 33/28* | (2006.01) |

(52) U.S. Cl.
CPC .............. *G01N 27/07* (2013.01); *E21B 47/102* (2013.01); *G01N 33/2823* (2013.01)
USPC ................... 702/7; 702/10; 702/12; 702/179

(58) Field of Classification Search
USPC ................... 702/7, 10, 12, 47, 100, 179, 182; 33/215; 73/152.18; 356/436
See application file for complete search history.

(56) References Cited

U.S. PATENT DOCUMENTS

| | | | |
|---|---|---|---|
| 3,009,095 A | 11/1961 | Noik | |
| 3,530,711 A | 9/1970 | Tocanne | |

(Continued)

FOREIGN PATENT DOCUMENTS

| | | |
|---|---|---|
| CN | 1147090 A | 4/1997 |
| CN | 2909250 Y | 8/2007 |

(Continued)

OTHER PUBLICATIONS

PCT/GB2008/001979 International Search Report; International Filing Date Jun. 6, 2008

(Continued)

Primary Examiner — Eliseo Ramos-Feliciano
Assistant Examiner — Felix Suarez
(74) Attorney, Agent, or Firm — GE Global Patent Operation (57) ABSTRACT

An apparatus for determining the concentration of a conductive fluid present in a fluid filled bore hole is described. Such apparatus are known as water hold-up meters and are frequently used in oil, gas and water filled bore holes. In bore hole applications, data bandwidth between a down hole device and the surface can be limited, while determining water hold-up based on down hole measurements can be data intensive. A technique is proposed for calculating the water hold up that requires less data to be transmitted between the down hole device and the surface.

18 Claims, 4 Drawing Sheets

(56) References Cited

U.S. PATENT DOCUMENTS

| | | | |
|---|---|---|---|
| 3,792,347 A | | 2/1974 | Hawley |
| 3,909,603 A | * | 9/1975 | Nicolas ..................... 702/12 |
| 4,216,536 A | | 8/1980 | More |
| 4,779,353 A | * | 10/1988 | Lopes et al. ................ 33/315 |
| 5,033,289 A | | 7/1991 | Cox |
| 5,297,425 A | * | 3/1994 | Hamby et al. ............. 73/152.18 |
| 5,739,637 A | | 4/1998 | Boettcher |
| 6,028,307 A | | 2/2000 | Young |
| 6,258,222 B1 | * | 7/2001 | Nakamura et al. ............ 204/242 |
| 6,393,925 B1 | * | 5/2002 | Devlin ...................... 73/861.05 |
| 6,507,401 B1 | * | 1/2003 | Turner et al. ................. 356/436 |
| 6,711,947 B2 | * | 3/2004 | Maute ....................... 73/152.29 |
| 6,722,207 B1 | * | 4/2004 | Feller ....................... 73/861.12 |
| 7,122,152 B2 | * | 10/2006 | Lewis et al. .................... 422/50 |
| 7,878,242 B2 | * | 2/2011 | Gray ....................... 166/250.13 |

FOREIGN PATENT DOCUMENTS

| | | |
|---|---|---|
| EP | 1428976 A2 | 6/2004 |
| GB | 2033630 A | 5/1980 |
| GB | 2396216 A | 6/2004 |

OTHER PUBLICATIONS

GB Search Report dated Nov. 5. 2007 from corresponding Application No. GB07 1096.8.

EP Office Action dated Dec. 17, 2012 from corresponding EP Application No. 08762316.1.

Unofficial English translation of CN Office dated Jan. 25, 2013 from corresponding CN Application No. 20080102136.6.

* cited by examiner

APPARATUS FOR DETERMINING THE CONCENTRATION OF A CONDUCTIVE FLUID PRESENT IN A FLUID FILLED BOREHOLE

CROSS-REFERENCE TO RELATED APPLICATIONS

This is a national stage application under 35 U.S.C. §371(c) of prior-filed, co-pending PCT patent application serial number PCT/GB2008/001979, filed on Jun. 6, 2008, which claims priority to Great Britain patent application serial number GB0711096.8, filed on Jun. 8, 2007, each of which is hereby incorporated herein by reference in its entirety.

BACKGROUND OF THE INVENTION

1. Field of the Invention

The invention relates to an apparatus for determining the concentration of a conductive fluid present in a fluid filled borehole, and in particular to devices known as water hold-up meters that are used in oil, gas and water filled bore holes.

2. Related Art

When drilling for and extracting hydrocarbons such as oil and gas, water can also enter the well and flow in the bore hole or drill pipe. It is desirable to understand the relative proportions of water and hydrocarbons in the well, so that the well yield can be understood, and informed decisions taken about well operation and maintenance. If a cross section of the well bore perpendicular to the well axis is considered then the proportion of the cross sectional area occupied by water in relation to the total cross sectional area is known as the water hold-up. Gas hold up or oil hold up can be calculated in a similar manner.

Figure 1A:
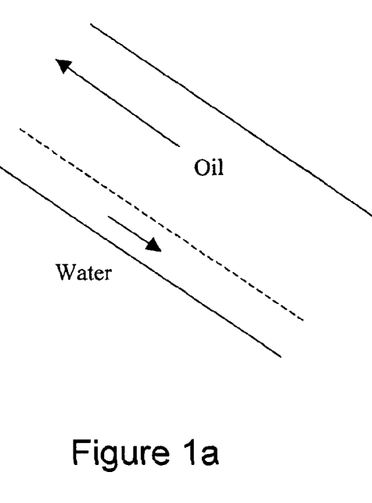
FIG. 1a is a longitudinal cross-section through a pipe or bore hole showing the flow of oil and water.
Figure 1B:
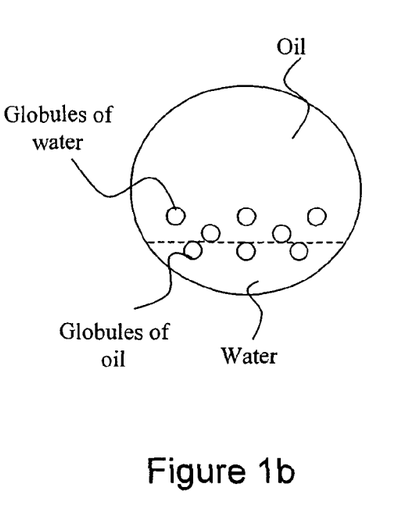
FIG. 1b is a transverse cross-section through a drill pipe showing the lateral separation of the water and oil layers.

Water and hydrocarbons do not readily form a solution. Instead, the smaller constituent fluid appears as globules within the majority fluid. The globules may be very small, as in an emulsion, or be very large resulting in total separation into layers, or alternating flow known in the art as slug flow. In a pipe line or bore hole that is non-vertical, the lighter fluids will tend to be more concentrated along the upper side of the pipe or hole. Lighter fluids will also tend to flow faster in an upward direction than the heavier ones, even to the extent that particular fluids may move in the opposite direction to the general flow. This is illustrated by way of example in FIGS. 1a and 1b. FIG. 1a is a longitudinal cross-section through a pipe or bore hole showing the lighter hydrocarbons such as oil rising rapidly against the downward flow of water. FIG. 1b is a transverse cross-section, through the pipe shown in FIG. 1a, showing the lateral separation of water and oil, as well as a layer in which globules of water are present in the oil, and globules of the oil are present in the water.

A resistance based water hold up meter works by sensing the apparent resistance of the fluid in the bore hole or drill pipe at an array of points across the area of the bore hole. Any water present will generally contain sufficient salts to make it significantly lower in resistivity than the hydrocarbons. The hydrocarbons on the other hand have a very low conductivity, and will appear mostly insulating. By measuring the resistance at different points across the bore hole, a clearer view of the proportion of water to hydrocarbons can be obtained. Furthermore, the monitored resistances as they vary with position and time, can be interpreted to improve understanding of the composition of the fluid in the bore hole.

U.S. Pat. No. 5,736,637 discloses a known device for evaluating the multiphase flow of fluid down-hole in a borehole.

U.S. Pat. No. 3,792,347 describes the use of largely insulated needle probes to spear oil globules such that the small exposed tip of the electrode loses its electrical path to ground through a predominantly water based fluid while within the globule, leading to a determination of the proportion of oil in the fluid.

U.S. Pat. No. 3,009,095 similarly describes using the resistive property to detect water globules in a predominantly oil based fluid by positioning two electrodes close to each other such that small globules of water between them creates a conductive path.

In order to generate sufficient or reliable data describing the fluid composition in the bore hole, it is desirable to take measurements continuously at a plurality of locations across the bore hole. The rate at which individual measurements of resistance are made by an individual resistance sensor is often several thousand times per second, and a single device often has a plurality of sensors. During the deployment of the device in the bore hole, a large amount of data can therefore be collected, subsequently needing to be processed and stored. Although the data can be stored in the device for later analysis, it is preferable to transmit the data to the surface for immediate analysis so that real time monitoring and decision making can occur. This allows the device to make a second pass through an area of interest immediately, rather than returning the device to the area after completion of an entire run. Transmission of data of this magnitude is effected using a wire-line connection, an electronic connection common in the art, between the surface and the device deployed in the bore hole. The limited capacity of the wire-line to transmit data therefore acts like a bottle neck in the amount of data that can be passed from the device to the surface. Alternatively, the data may be recorded in-situ in the borehole and similarly the capacity of the recording medium may represent a bottle neck between the instrument and the eventual presentation of the data.

In order to maintain sufficient measurement range and resolution it is typical that the measured resistance will be measured across at least 16 binary digits on a logarithmic scale. Given that a resistance value will typically be represented as a 16 bit number (giving approximately 66,000 possible resistance values) and assuming that the sampling occurs at a frequency of say 5 kHz, the wire-line connection from the device to the surface will need to transmit 80 kbs of data per sensor. For a device having 12 sensors, a wire-line connection supporting a bandwidth of nearly 1 Mb/s is then required. However, typical transmission links have a limited bandwidth perhaps in the order of 25 kb/s to 100 kb/s, and often shared with other instruments. We have therefore appreciated that there is a need for an improved device allowing more efficient collection and processing of the water hold-up data to work with commonly available transmission links.

SUMMARY OF THE INVENTION

The invention is defined in the independent claims to which reference should now be made. Advantageous features are set out in the dependent claims.

BRIEF DESCRIPTION OF THE DRAWINGS

The invention will now be described in more detail by way of example and with reference to the drawings in which.

DETAILED DESCRIPTION OF THE INVENTION

In bore hole applications, data bandwidth between a down hole device and the surface can be limited, while determining water hold-up based on down hole measurements can be data intensive. A technique is proposed for calculating the water hold up that requires less data to be transmitted between the down hole device and the surface.

Figure 2:
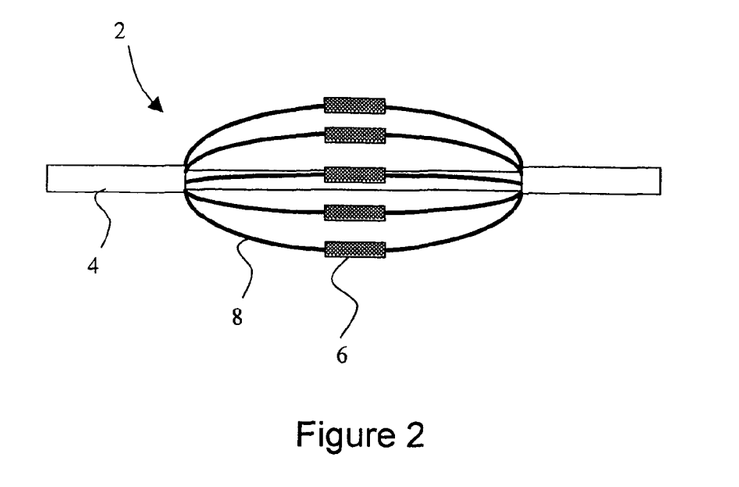
FIG. 2 is a side elevation view of a preferred device for deployment in the bore hole to determine water hold-up.

Referring to FIG. 2, a device will now be described for determining the concentration of a conductive fluid in a fluid filled bore hole according to a preferred embodiment of the invention. Throughout the description and claims, the terms conductive fluid and substantially non-conductive fluids will be used to refer to water or water-like fluids on the one hand, and hydrocarbons or hydrocarbon-like fluids on the other.

Figure 3:
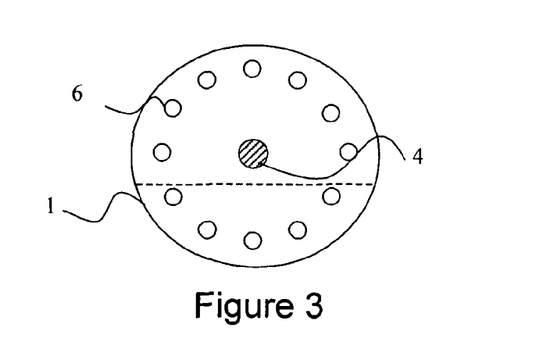
FIG. 3 is a cross-sectional view through the borehole showing the arrangement of electrodes provided by the device of FIG. 2.

FIG. 2 is a side elevation view of a water hold up meter 2. The instrument comprises a central rod or mandrel 4 for connection with a down-hole tool string (not shown). A number of resistance probes 6 or sensors are mounted on the mandrel by respective bow springs 8. In the preferred embodiment shown, the bow springs are mounted around the circumference of the mandrel so that the resistance probes form a circular array that follows the periphery of the bore hole or the pipe line 1 in which the device is located. This is illustrated in FIG. 3.

Figure 4:
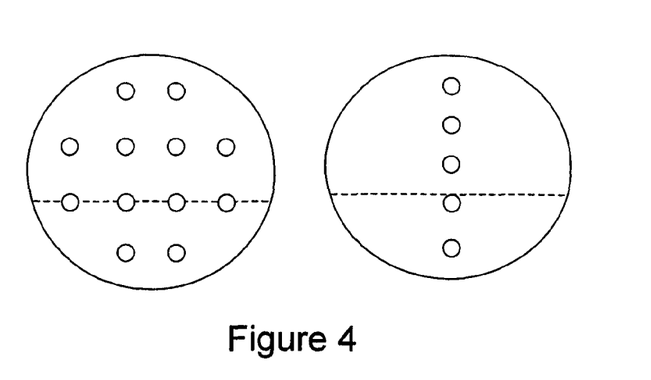
FIG. 4 illustrates alternative possible configurations of electrodes in the bore hole.

The resistance sensors or probes may be arranged differently, such as the matrix or linear arrangements shown in FIG. 4. As the fluids in the pipe are sometimes stratified, the linear arrangement can give good results providing it is angled correctly with respect to the fluid layers. The matrix arrangement gives a fuller view of the fluid composition in the pipe, but is more costly in terms of manufacture and the amount of data obtained. The arrangement of electrodes around the periphery shown in FIG. 3 is therefore a good compromise between the two. The structure of devices having sensor arrays like those shown in FIG. 4 will likely differ from that shown in FIG. 2 because of the need to support a sensor in the middle of the pipe, or in a lattice-like array. However consideration of such structures is not necessary for an understanding of the invention.

Figure 5:
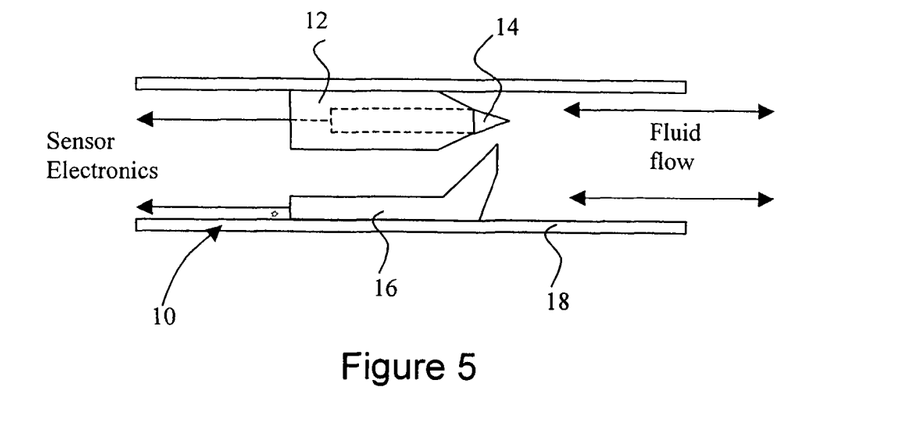
FIG. 5 is a schematic illustration of one of the resistance sensors in more detail.

An individual resistance probe or sensor is illustrated in FIG. 5. The sensor 10 comprises a housing 12 made of insulating material. A sensor electrode 14 is mounted in the housing 12 such that it is insulated from the reference electrode 16, and except for its tip, from the fluid. The sensor electrode has a tapered or conical tip which is not insulated from the fluid, by means of which the measurement is made. The tip is orientated so that in operation it is substantially parallel to a first direction along which the fluid in the bore hole is caused to flow. This ensures that the tip pierces or bursts any fluid globules within the fluid and improves the overall accuracy of the measurement.

Signals are passed from the respective electrodes to sensor electronics in the device. The reference contact is typically at earth potential. The spacing of the electrodes determines the minimum size of conductive globule that can be detected in a predominantly insulating fluid. The area of the exposed sensor electrode determines the minimum size of insulating globule that can be detected in a predominantly conductive fluid. The reference electrode 16 is ramp shaped, having an angled portion that extends from the casing 18 towards the tip of the active electrode 14.

Figure 6:
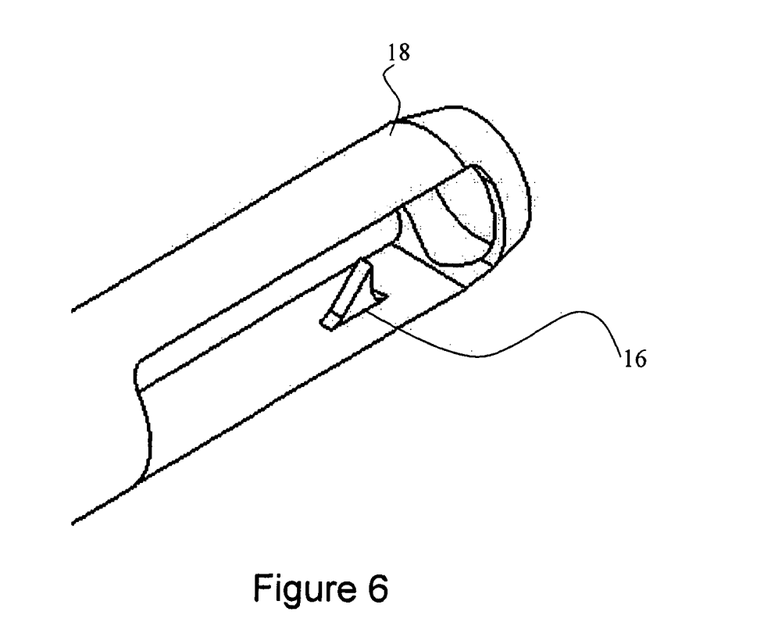
FIG. 6 is an isometric view of the reference electrode and casing shown in FIG. 5.

The casing 18 is preferably provided in the form of a cylindrical shield having an opening at least one end, so that fluid can flow directly onto the tip of the sensor electrode (from right to left) in a preferred fluid direction. Fluid can then escape at the side of the shield or housing. In another example, the shield has openings at the ends or sides both upstream and downstream of the electrodes. The housing therefore defines at least first and second fluid flow directions, that are substantially opposite to each other. Of course, the reference electrode may be angled such that the first and second directions are not opposite, if the desired geometry of the sensor dictates. An isometric view of the casing and reference electrode is shown in FIG. 6; the active or sensor electrode is positioned along the axis of the casing above the reference electrode.

The spacing of the sensors determines the minimum size of water globules in oil that can be recognised. A small spacing is good, but too small a spacing might result in a globule being caught by the sensor probes, and obscuring subsequent changes in fluid composition.

Fluid flowing onto the sharp parts of the electrodes helps to break down globules in the fluid. Hence, the sensor probes are provided with sharp edges in at least one direction of flow (from right to left in the diagram). Furthermore, globule bursting in the opposite direction is helped by angling one of the electrodes into the fluid flow, the ramp or wedge-shaped reference electrode 16 in this case, to direct the flow laterally across the sharp tapered tip of the other electrode to assist in breaking through the globule boundaries. Thus the reference electrode acts like a spoiler. This improves the symmetry of the response between the two directions at low flow rates.

In operation, a potential is applied to the sensor electrode so that a current is induced in the fluid between the electrodes. The current may be detected at either of the electrodes, and from the measured current and the known potential, the resistance of the incident fluid can be determined.

Figure 7:
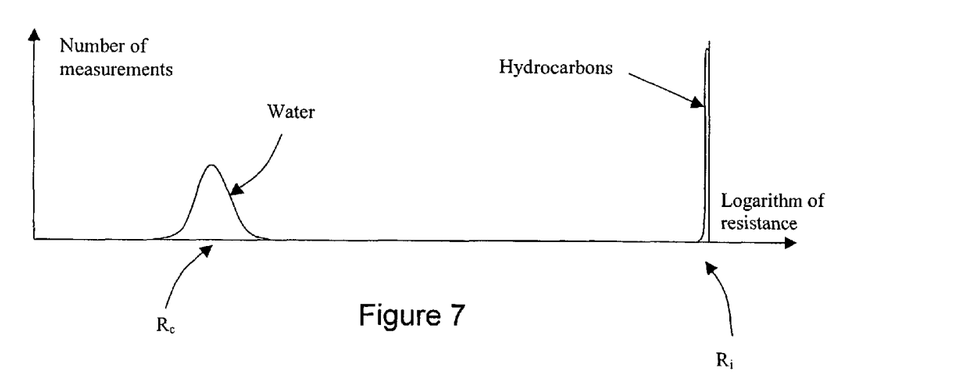
FIG. 7 is a graph illustrating the likely distribution of resistance measurements obtained from a bore hole containing both water and hydrocarbons.

In practice, the range of resistances detected by the sensor will be very large. The water flowing the in the pipe will have a relatively low resistance due to its salt content, while the hydrocarbons will have very high resistance and will act like an insulator. As a result of this, it is preferred to use the logarithms of the resistance values because of the large possible range of values. Furthermore, the values detected by the sensor are preferably scale limited, so that the very high or infinite resistances of the hydrocarbons can be accommodated. Running a sensor over a period of time will therefore produce a distribution of values like that shown in FIG. 7. The graph shows two separate peaks: a broader peak for low resistance values representing a range of resistances measured for the conducting fluid, namely the water, as well as a narrow high peak representing the high resistances possibly limited by sensor scale for the non-conducting fluids or hydrocarbons.

The operation of the preferred embodiment will now be described in more detail.

The sampled values of resistance are found to fall into one of two tight clusters with a distribution of values at a mean of $R_i$ for oil or gas, and $R_c$ for water. $R_c$ is therefore the apparent resistance of the conductive fluid, namely the water, and $R_i$ is the apparent resistance of the insulting fluid, namely the hydrocarbons. The term apparent resistance is used here to reflect the fact that the resistance of the water or hydrocarbons is not a static property but changes over time as the flow and properties of the constituent bore hole fluids change, and because it is further affected by the sensor geometry and interferences to the sensor, for example surface wetting, debris or corrosion.

As the clusters are tight, we can assume to a good approximation that all resistance measurements of oil and water result in a reading of $R_i$ and $R_c$. The proportion of samples at $R_c$, compared with the proportion at $R_i$, will then reflect the proportion of water by volume in the fluid as a whole. Assuming that $N_c$ is the number of samples at $R_c$ and $N_i$ is the number of samples at $R_i$, then the water hold-up, h, can be defined as the volume proportion of water in the fluid so that:

$$h = N_c/(N_c+N_i)$$

It is easily shown that:

$$1-h = N_i/(N_c+N_i)$$

The mean, m, of a set of n values (R) is $$m = \Sigma(R)/n$$

Applying this to the measured fluid, $$m = (N_c R_c + N_i R_i)/(N_c+N_i)$$

and substituting the above expressions for h and (1−h), this can be written:

$$m = h \cdot R_c + (1-h) \cdot R_i \qquad [1]$$

If both $R_c$ and $R_i$ are known, the water hold up h, can be derived directly from expression 1, according to:

$$h = (m-R_i)/(R_c-R_i)$$

It will be understood to one skilled in the art of borehole data logging that monitoring the value of m over long periods or large axial distances along the pipe in many circumstances will reveal the values or Ri and Rc. This is because the maximum and minimum possible values of m will occur when the sensor is presented with pure hydrocarbon or pure water. These maximum/minimum excursions can be considered to be Rc and Ri. It is understood that this will not always be the case.

The standard deviation, sd, of a set of values R is given by:

$$sd = \sqrt{\left[\sum ((R-m)^2)/n\right]}$$
$$= \sqrt{\left[\sum (R^2 - 2mR + m^2)/n\right]}$$
$$= \sqrt{\left[\sum (R^2)/n - \sum (2mR)/n + \sum (m^2)/n\right]}$$
$$= \sqrt{\left[\sum (R^2)/n - 2m\sum (R)/n + n(m^2)/n\right]}$$
$$= \sqrt{\left[\sum (R^2)/n - 2m^2 + m^2\right]}$$
$$= \sqrt{\left[\sum (R^2)/n - m^2\right]}$$

Applying this to the measured fluid:

$$sd = \sqrt{[(N_c(R_c^2) + N_i(R_i^2))/(N_c+N_i) - m^2]} \qquad [2]$$
$$= \sqrt{[h(R_c^2) + (1-h)(R_i^2) - m^2]}$$

We can then use equations [1] and [2] to eliminate $R_c$. From [1], $$R_c = (m-(1-h)R_i)/h$$

Substituting in [2], $$sd = \sqrt{[h(((m-(1-h)R_i)/h)^2) + (1-h)(R_i^2) - m^2]}$$
$$= \sqrt{[(m-(1-h)R_i)^2/h + (1-h)(R_i^2) - m^2]}$$
$$= \sqrt{\begin{array}{l}[(m^2 + (1-h)^2 R_i^2 - 2m(1-h)R_i)/h + \\ (1-h)(R_i^2) - m^2]\end{array}}$$
$$= \sqrt{\begin{array}{l}[m^2/h + (1-h)^2 R_i^2/h - 2m(1-h)Ri/h + \\ (1-h)(R_i^2) - m^2]\end{array}}$$
$$= \sqrt{\begin{array}{l}[m^2(1/h-1) + R_i^2(1/h+h-2+1-h) - \\ 2m(1-h)R_i/h]\end{array}}$$
$$= \sqrt{\begin{array}{l}[m^2(1/h-1) + Ri^2(1/h-1) - \\ 2m(1/h-1)R_i]\end{array}}$$

$$\frac{sd^2}{(1/h-1)} = m^2 + R_i^2 - 2mR_i$$
$$= (R_i - m)^2$$

If we define $$x = (Ri-m)^2$$

$$sd^2/(1/h-1) = x$$

$$h \cdot sd^2 = x(1-h)$$

$$h(sd^2+x) = x$$

$$h = x/(sd^2+x)$$

Thus, a value for the water hold up h can then be calculated from expressions [1] and [2] for the mean and standard deviation, as follows:

Hold up $h = x/(x+sd^2)$, where $x = (R_i-m)^2$ [3]

For each sensor, the average value m and the standard deviation sd are therefore calculated. The sampling period over which the average is taken must be long compared with the natural variations in the fluid flow regime. Typically ⅓ of a second is preferred, with a sampling rate of about 400 samples for each of the 12 sensors. The period or sampling rate could be changed by a factor of two if more/less data is required.

The values m and sd are then transmitted to the surface via the wire-line, so that the hold up h can be calculated using a predetermined value for $R_i$. $R_i$ can be determined from the bore hole fluid, by observation of the variation in values of m and sd for a given sensor and noting the value of m when it is high, and accompanied by a low value of sd. This can be done at the surface for a period of time before measurement of water hold up takes place. It will be appreciated that $R_c$ could be used instead of $R_i$. In this case, $$h = sd^2/(sd^2+(m-R_c)^2)$$

However, $R_i$ is preferred as the hydrocarbon end of the readings tends to give a tighter distribution and be less variable.

Because the resistivity of a typical hydrocarbon fluid is practically infinite, the detection circuit in the sensor will either limit the measured $R_i$ to the maximum resistance value permitted, or will report a slightly lower value reflecting the presence of contaminants on the probe. Providing these contaminants still have a very high resistance compared with the water in the well, the accuracy of the method is not affected. What is important is that the values for the insulating fluid are clear of the distribution for the conducting fluid and that the distributions are tight.

The calculation of the hold up h from the mean and standard deviation relies on the recognition that the distribution is predominantly bipolar, and the mean value ($R_i$ in this case) of the tighter cluster being known. Provided the two clusters each have a standard deviation less than 20% of the separation between their two means, the resulting contribution to the error in the hold up calculation is less than 4%.

The nature of the distribution can however change with changing conditions in the well, for example, different constituents, and with changing depth.

A bipolar distribution has a standard deviation that reduces as the mean value moves towards either end of its working range. When the standard deviation is at its lowest value at one end, the associated mean can be used to calculate the value for the hold up using the expression given above.

For this reason, it is preferred that only the mean and standard deviation are transmitted to the surface, so that they can be used to confirm the suitability of the approximation, as well as aiding in the recognition and interpretation of other conditions. Thus, it is never necessary to transmit the measured resistance values themselves.

It will be appreciated that in the preferred embodiment, the sensor is provided with 12 sensors, located at different points in the bore hole. In practice therefore, 24 values are transmitted along the wire-line connection each sampling period. This gives a considerable reduction in bandwidth usage.

It can also be shown that the mean and standard deviation of the bipolar distribution can be used with $R_i$ to calculate $R_c$, or alternatively with $R_c$ to calculate $R_i$.

$$R_c = (m \cdot R_i - m^2 - sd^2)/(R_i - m)$$

$$R_i = (m^2 + sd^2 - m \cdot R_c)/(m - R_c)$$

This is likely to be useful, for example, where $R_i$ is fixed at the upper limit of the measurement range and some visibility of the resistance of the conductive fluid, $R_c$, is desired. However it is more reliant on a bipolar nature of distribution than the calculation for hold up.

Although, the operation of the device has been explained in terms of measuring the resistance of the fluid, the explanation is intended to include measurement of conductance, the reciprocal of resistance. References to resistance are not therefore intended to exclude conductivity. Indeed the use of mean and standard deviation as a means of providing data compression can be applied to other values sampled from predominantly bipolar distributions, for example capacitance or density.

The preferred technique advantageously makes use of the realisation that the time average value of the parameter we are measuring (in this case resistance of conductance) can be assumed to be the weighted sum of two constants, and further that the value of water hold up sought is given by the weighting. The weighting itself is revealed by the standard deviation and mean. The weighting or hold up can be a result of the fluids being mixed or because the parameter measured varies rapidly between two extremes and is time averaged to the same effect.

Figure 8:
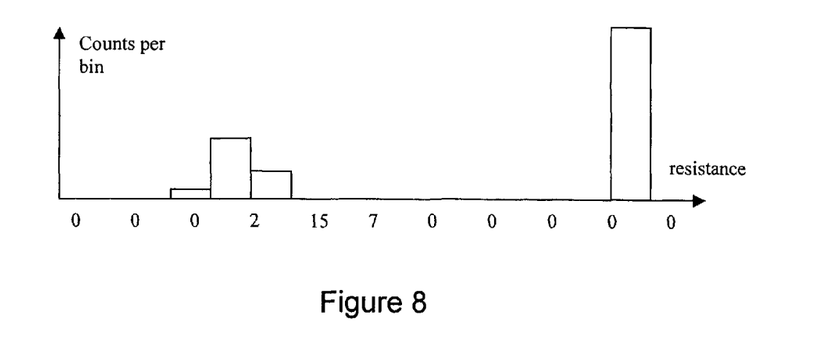
FIG. 8 is a histogram illustrating processed results in a second preferred method.

In a second preferred embodiment, a reduction in data transmitted from the device to the control systems at the surface is achieved by transmitting a histogram of data. The reading of resistance obtained from each probe is allocated to one of a number of predetermined, exclusive ranges of values. Each range essentially forms a 'bin' or category, and for each measured value falling into the range during a given sampling period, a count is added to the value of the bin. Each bin starts with an initial value of zero. The device is then configured to transmit the number of counts in each bin to the surface control systems for further processing. An example of the output produced is illustrated in FIG. 8. Using the histogram of data, the mean and standard deviation can be determined approximately, and the water hold up calculated using the equations above. In practice though, the counts in each cluster, $N_c$ and $N_i$ would be used directly so that the water hold up would be $N_c/(N_c+N_i)$. The transfer of the histogram information requires more data to be transmitted than the first approach. However, it is advantageous in that the view of hold-up can be understood visually from the histogram itself as well as the distribution of the conductive part of the fluid. This means that when encountering a more complex fluid mixture with say three or more histogram peaks a reasonable quantitative evaluation of the hold-up can still be calculated.

The first technique of transmitting mean and standard deviation can also be combined with occasionally transmitting a histogram. The value of R (for $R_i$ or $R_c$) could then be taken from the histogram. Alternatively if the constituent fluids in the bore hole are known, then the value of R might already be known. In this case, calculation of the water hold up h could be based solely on m and sd, with the input of $R_c$ or $R_i$ purely as a known value (constant for the calculation).

In a further alternative embodiment, the calculation of the hold up h could be calculated in the tool itself. However, in order to do that, a control process implementing rules for ensuring the standard deviation and mean belong to a sufficiently bipolar distribution must be provided in the tool if the accuracy of the technique is to be maintained. The data obtained could be stored in the tool for subsequent analysis, but as noted above it is preferred if the data is transmitted to the surface by wire-line, so that immediate analysis can be made.

Although, the transmission link is typically provided by means of a wire-line or cable, other transmission methods could be used with the invention, such as wireless connections, if these were available. Alternatively, the data may be recorded locally to the instrument for retrieval at a later time.

The invention claimed is:

1. An apparatus for determining the proportion of a conductive fluid within a mix of fluids in a fluid-filled borehole, the apparatus comprising:
   one or more resistance probes for measuring the resistance of a borehole fluid with which they are in contact;
   a processor arranged to:
   a) receive resistance measurements from the resistance probes; and
   b) calculate for a measurement time period the mean (m) and standard deviation (sd) of the resistance measurements; and
   a transmitter arranged to transmit the calculated mean and standard deviation to a receiver at a second location, wherein the receiver outputs the mean and standard deviation to a second processor arranged to calculate the concentration of conductive fluid within a mix of fluids in the fluid filled borehole from the mean and standard deviation, and a predetermined value of R based on resistance.

2. The apparatus of claim 1, wherein the second processor is arranged to determine from the resistance measurements, the apparent resistance R of either the substantially conductive ($R_c$) or substantially non-conductive fluids ($R_i$).

3. The apparatus of claim 1, wherein the value of R is known, and wherein in the calculation by the second processor, the value of R is required to be input.

4. The apparatus of claim 1, wherein the second processor is arranged to calculate the water hold up value (h), according to the equations 1 and 2:

$$h = x/(x+sd^2), \text{ and} \quad [1]$$

$$x = (R_i - m)^2; \quad [2]$$

where sd is the standard deviation of the resistance measurements, m is the mean value of the resistance measurements and Ri is the apparent resistance value of the fluids in the borehole that are substantially non conductive, averaged over the measurement time period; or according to equation 3

$$h = sd^2/(sd^2 + (m-R_c)^2) \quad [3]$$

where sd is the standard deviation of the resistance measurements, m is the mean value of the resistance measurements, and $R_c$ is the apparent resistance value of the fluids in the borehole that are substantially conductive.

5. The apparatus of claim 4, wherein only the values of m and sd are transmitted to the receiver at the second location.

6. The apparatus of claim 5, comprising a wire-line connection between the transmitter and receiver for transmitting the calculated values.

7. The apparatus of claim 6, wherein the second processor is located at the surface of the borehole.

8. An apparatus for determining the resistance of one fluid within a mix of fluids in a fluid-filled borehole, the apparatus comprising:
one or more resistance probes for measuring the resistance of a borehole fluid with which they are in contact;
a processor arranged to:
a) receive resistance measurements from the resistance probes; and
b) calculate for a measurement time period the mean (m) and standard deviation (sd) of the resistance measurements; and
a transmitter arranged to transmit the calculated mean and standard deviation to a receiver at a second location, wherein the receiver outputs the mean and standard deviation to a second processor arranged to calculate the resistance of one fluid within a mix of fluids in the fluid filled borehole from the mean and standard deviation and a predetermined value R based on resistance for the other fluid or fluids within the mix.

9. The apparatus of claim 8, wherein the second processor is arranged to calculate the resistance value for the substantially conductive fluid within the mixture, according to the equation:

$$R_c = (m \cdot R_i - m^2 - sd^2)/(R_i - m)$$

or the resistance value for the substantially non conductive fluid within the mixture, according to the equation:

$$R_i = (m^2 + sd^2 - m \cdot R_c)/(m - R_c)$$

where sd is the standard deviation of the resistance measurements, m is the mean value of the resistance measurements, $R_c$ is the apparent resistance value of the fluids in the borehole that are substantially conductive, and $R_i$ is the apparent resistance value of the fluids in the borehole that are substantially non conductive, averaged over the measurement time period.

10. An apparatus for determining the concentration of a conductive fluid within a mix of conductive and non-conductive fluids in a fluid-filled borehole, the apparatus comprising:
one or more resistance probes for measuring the resistance of a borehole fluid with which they are in contact; and
a processor arranged to:
a) receive resistance measurements from the resistance probe;
b) calculate for a measurement time period a mean and a standard deviation of the resistance measurements; and
c) using the mean and standard deviation, and a predetermined value of R based on resistance, calculate the concentration of conductive fluid within a mix of fluids in the fluid filled borehole.

11. An apparatus for determining the concentration of a conductive fluid within a mix of conductive and non-conductive fluids in a fluid-filled borehole, the apparatus comprising:
one or more resistance probes for measuring the resistance of a borehole fluid with which they are in contact; and
a first processor arranged to receive resistance measurements from the resistance probes, and to assign each resistance measurement according to its value to one of a plurality of measurement bins, wherein each measurement bin corresponds to a range of resistance measurement values, wherein the first processor is further arranged to:
a) receive resistance measurements from the one or more resistance probe;
b) calculate for a measurement time period a mean (m) and standard deviation (sd) of the resistance measurements; and
c) transmit the number of measurements assigned to each measurement bin, the resistance measurements, the mean and the standard deviation to a second processor, wherein the second processor is arranged to calculate the concentration of the conductive fluid within a mix of fluids in the fluid filled borehole from the numbers of measurements in each measurement bin, and from the mean and standard deviation, and a predetermined value of R based on resistance.

12. An apparatus for determining the concentration of a conductive fluid within a mix of conductive and non-conductive fluids in a fluid filled borehole, the apparatus comprising:
at least one resistance probe for determining the resistance of a borehole fluid with which they are in contact, the at least one resistance probe comprising a sensor electrode and a reference electrode;
wherein the sensor electrode has a tapered portion that is exposed to the fluid for taking a measurement of resistance, the tapered portion of the sensor electrode arranged to face a first fluid flow direction; and wherein the reference electrode cooperates with the sensor electrode so that in a second fluid flow direction the fluid flow is deflected towards the tapered portion of the sensor electrode; and
a processor arranged to:
a) receive resistance measurements from the at least one resistance probe; and
b) calculate for a measurement time period the mean (m) and standard deviation (sd) of the resistance measurements; and
a transmitter arranged to transmit the calculated mean and standard deviation to a receiver at a second location, wherein the receiver outputs the mean and standard deviation to a second processor arranged to calculate the concentration of conductive fluid within a mix of fluids in the fluid filled borehole from the mean and standard deviation, and a predetermined value of R based on resistance.

13. The apparatus of claim 12, wherein the first and second fluid flow directions are substantially opposite to each other.

14. The apparatus of claim 12, wherein the first and second electrodes are mounted within a fluid communicable housing, and wherein the housing defines at least first and second fluid flow directions.

15. The apparatus of claim 12, wherein the reference electrode has a surface extending into fluid flow, the surface being angled towards the tapered portion of the sensor electrode.

16. The apparatus of claim 15, wherein the reference electrode is wedge-shaped and mounted on the housing.

17. An apparatus for determining the resistance of one fluid within a mix of conductive and non-conductive fluids in a fluid-filled borehole, the apparatus comprising:
- at least one resistance probe for measuring the resistance of a borehole fluid with which they are in contact; and
- a processor arranged to:
  a) receive resistance measurements from the resistance probes;
  b) calculate for a measurement time period the mean and standard deviation of the resistance measurements; and
  c) using the mean and standard deviation, and a predetermined value R based on resistance for one of the fluids, calculate the resistance value for the other fluid or fluids within a mix of fluids in the fluid filled borehole.

18. An apparatus for determining the resistance of one fluid within a mix of conductive and non-conductive fluids in a fluid-filled borehole, the apparatus comprising:
- at least one resistance probes for determining the resistance of a borehole fluid with which they are in contact, the at least one resistance probe comprising a sensor electrode and a reference electrode;
- wherein the sensor electrode has a tapered portion that is exposed to the fluid for taking a measurement of resistance, the tapered portion of the sensor electrode arranged to face a first fluid flow direction; and wherein
- the reference electrode cooperates with the sensor electrode so that in a second fluid flow direction the fluid flow is deflected towards the tapered portion of the sensor electrode;
- a processor arranged to:
  a) receive resistance measurements from the at least one resistance probe; and
  b) calculate for a measurement time period the mean (m) and standard deviation (sd) of the resistance measurements; and
- a transmitter arranged to transmit the calculated mean and standard deviation to a receiver at a second location, wherein the receiver outputs the mean and standard deviation to a second processor arranged to calculate the concentration of conductive fluid within a mix of fluids in the fluid filled borehole from the mean and standard deviation, and a predetermined value of R based on resistance.

* * * * *